(12) United States Patent
Mohanty et al.

(10) Patent No.: US 9,089,698 B2
(45) Date of Patent: Jul. 28, 2015

(54) METHOD AND APPARATUS FOR OPTOGENETIC TREATMENT OF BLINDNESS INCLUDING RETINITIS PIGMENTOSA

(75) Inventors: Samarenda K. Mohanty, Irvine, CA (US); Matthew Ficinski, Baldwin Park, CA (US); Edward K. Wong, Newport Beach, CA (US); Michael W. Berns, Bonsall, CA (US)

(73) Assignee: The Regents of the University of California, Oakland, CA (US)

( * ) Notice: Subject to any disclaimer, the term of this patent is extended or adjusted under 35 U.S.C. 154(b) by 377 days.

(21) Appl. No.: 12/760,520

(22) Filed: Apr. 14, 2010

(65) Prior Publication Data
US 2010/0268150 A1 Oct. 21, 2010

Related U.S. Application Data

(60) Provisional application No. 61/170,357, filed on Apr. 17, 2009.

(51) Int. Cl.
| | |
|---|---|
| *A61N 1/32* | (2006.01) |
| *A61N 1/04* | (2006.01) |
| A61F 9/00 | (2006.01) |
| A61K 9/00 | (2006.01) |
| A61K 38/17 | (2006.01) |

(52) U.S. Cl.
CPC .............. *A61N 1/327* (2013.01); *A61N 1/0412* (2013.01); *A61F 9/0017* (2013.01); *A61K 9/0048* (2013.01); *A61K 38/177* (2013.01); *A61N 1/0416* (2013.01)

(58) Field of Classification Search
CPC ............................. A61N 1/327; A61N 1/0412
See application file for complete search history.

(56) References Cited

U.S. PATENT DOCUMENTS

2007/0053996 A1 * 3/2007 Boyden et al. ................. 424/718

FOREIGN PATENT DOCUMENTS

| WO | WO 2006/123248 | * 11/2006 |
|---|---|---|
| WO | WO 2007/148038 | * 12/2007 |

OTHER PUBLICATIONS

Dezawa et al., 2002, Micron, 33: 1-6.*
Sekirnjak et al., 2006, J. Neurophysiol., 95: 3311-3327.*
Cayouette et al., 1997, Human Gene Therapy, 8: 423-430.*

* cited by examiner

*Primary Examiner* — Marcia S Noble
(74) *Attorney, Agent, or Firm* — Marcus C. Dawes; Daniel L. Dawes

(57) ABSTRACT

An apparatus for in vivo electroporating a plasmid into a retina of any eye includes a first electrode with a first polarity of voltage placed in contact with a cornea of the eye, a second electrode with an opposite second voltage at least in part behind the retina, and a pulsed voltage source for providing a pulsed DC voltage with an optimized field strength amplitude, frequency, number of pulses, group repetition rate and duration of pulse and group repetition, which are optimized for transfection of the channelrhodopsin-2 (ChR2) gene into the retinal ganglion cells. An in vivo method for treating retinal ganglion cells in an eye without use of viral transfection includes the steps of nonviral in vivo delivering a channelrhodospsin-2 (ChR2) gene to target the specific (retinal ganglion) cells of a retina by intravitreous injection of plasmid DNA, electroporating the plasmid into the retina and use of image intensification device for stimulating the retinal ganglion cells with ambient lighting conditions.

4 Claims, 3 Drawing Sheets

METHOD AND APPARATUS FOR OPTOGENETIC TREATMENT OF BLINDNESS INCLUDING RETINITIS PIGMENTOSA

RELATED APPLICATIONS

The present application is related to U.S. Provisional Patent Application, Ser. No. 61/170,357, filed on Apr. 17, 2009, which is incorporated herein by reference and to which priority is claimed pursuant to 35 USC 119.

BACKGROUND OF THE INVENTION

1. Field of the Invention

The invention relates to the field of apparatus and methods for optogenetic treatment of blindness including retinitis pigmentosa.

2. Description of the Prior Art

Retinitis pigmentosa (RP) refers to disorders characterized by degeneration of photoreceptors in the eye which hinders visual ability by nonfunctional neuronal activation and transmission of signals to the cortex. The prevalence of this disease is at least one million individuals. The disease is most often inherited as an autosomal recessive trait with 50 to 60% of cases having this form of inheritance. However, since not all RP-causing genes have been discovered, if a person chooses to get genetically tested, there is about a 50 percent chance that the disease causing gene will be identified. Although there is no definitive nonsurgical therapy available for RP, numerous claims of therapeutic triumphs have been made in the United States and abroad within the last decade. Though an experimental 'rescue' of retinas by treating eyes with certain stem cells has been shown to preserve visual function in mice that were genetically predisposed to degenerative diseases of the retina, most of the current clinical treatments are primarily focused on slowing down the progression of the disease, as there is no cure that can stop the disease; there is no therapy that can restore any vision lost due to this disease.

The invasive surgical procedure for partial restoration of vision is by retinal implants/transplants. The subretinal implants are positioned in the area of the retina where the rod and cone photoreceptor cells reside, between the pigmented epithelium and the bipolar cells. The epiretinal implants are placed in the area of the retinal ganglion cells. The subretinal implants are composed of a 50-100 µm thin plate which is 2-3 mm in diameter and on this plate there is an array of microphotodiodes and microelectrodes. Light is detected by the microphotodiodes and then transformed into electrical currents which are delivered to neurons by the microelectrodes. The subretinal implants are surgically placed within the eye by entering the vitreous humor of the eye and making a scleral incision to gain access to the subretinal space. The disadvantages with using the subretinal implants also include the fact that the device undergoes damage over a period of time. Another disadvantage is that one microphotodiode will not be able to produce a current sufficient enough to stimulate adjacent neurons with the use of ambient light. In epiretinal implants, no light sensitive elements are used on the implant itself. The implant is placed in the same area where the retinal ganglion cells reside and the device functions by stimulating the axons of the retinal ganglion cells in response to input obtained from a camera that can be placed outside of the eye or within an intraocular lens. The use of an epiretinal implant requires that any visual information which is obtained by the camera will be translated into a spatiotemporal pattern of electrical stimuli. There are certain disadvantages to using this approach, primarily due to surgically implanting the device. It is difficult to place the device in the epiretinal space and if damage occurs during the implantation procedure, then cellular proliferation can occur. Furthermore, a disordered stimulation pattern can result while using epiretinal implants due to the fact that the electrical stimulation can stimulate both the axons and cell bodies of the ganglion cells. Currently, studies have been done on blind individuals with the use of epiretinal implants eliciting a response where the individuals were able to see patterns of light. However, the results have not been able to produce any object recognition in individuals.

Another invasive technique for treating retinitis pigmentosa involves the use of retinal transplants. Animal studies have been done which have shown some success in utilizing this approach. In one study, sheets of fetal retina with fetal pigment epithelium were transplanted into the subretinal space of rats. The experiment showed successful functioning of the retina through the recording of visually evoked responses that corresponded to the area where the transplant was placed. Furthermore, studies have been done on human subjects in which neural retinal progenitor cell layers with retinal pigment epithelium were transplanted into the eyes of a small number of patients having retinitis pigmentosa and age-related macular degeneration. Though results of the study showed that the visual acuity is improved in some of the patients, critical issues exists in transplantation of a larger number of tissue sheets into the retina.

Besides being highly invasive in nature, all the above methods for restoration of vision are based on very non-specific cellular activation and have low spatial resolution, and hence have not been very successful in restoration of vision.

The optogenetic treatment is based on a very recent phenomenon where chemically identical neurons can be activated by blue light with high temporal precision by introducing a light-activated molecular channel, named channelrhodopsin-2 (ChR2), into specific groups of cells by genetic targeting. This eliminates the highly challenging requirement of placing electrodes inside every single neuron of a chemically identified group of cells. This method also has several advantages over electrical stimulation such as cellular specificity. and noninvasiveness. Since ChR2 is a non-selective cation channel, light-induced activation of ChR2 results in depolarization of only those neurons that express ChR2. Selective activation of neurons by ms-pulsed blue light has been demonstrated in cell culture, brain slices, as well as in small animals. This optogenetic activation method is very attractive and practical as it only requires light of very low intensity (few mW/mm$^2$) that can be delivered from a lamp with a bandpass filter or small laser diode. Though this technique eliminates the highly challenging requirement of placing electrode arrays and it has advantages over electrical stimulation such as cellular specificity, higher resolution and non-invasiveness, transfection of a specific cellular layer in the retina requires efficient delivery of genes. Therefore, the only in vivo attempt for restoration of vision in blind mice models involves delivery of the ChR2 gene by the viral method. Besides the increasing concern about use of viruses, a ubiquitous CMV promoter was used, which is known to target non-specifically the whole retina. The recent promoter specific study targeting bipolar cells used in-utero electroporation, but it is not applicable for in-vivo applications. Further, since the spatiotemporal pattern of action potentials generated by retinal ganglion neurons ultimately determines the raw input from the eyes to the brain, specific targeting of retinal ganglion cells should provide a better and efficient method for restoration of vision.

Light-assisted activation of selected groups of neurons has been made possible with high temporal precision by introducing a light-activated molecular channel, named channelrhodopsin-2 (ChR2) into specific groups of cells by genetic targeting. This optogenetic activation method is very attractive and practical as it only requires light of very low intensity. Though this technique eliminates the highly challenging requirement of placing electrode arrays and has advantages over electrical stimulation such as cellular specificity and non-invasiveness, this optogenetic method requires transfection of specific cellular layer in retina. The viral method of delivery of the ChR2 coding gene has been primarily a concern for successful application of this technique. Related known prior art includes Miller G (2006) Shining new light on neural circuits. Science 314: 1674-1676. Bi, A., Cui, Ma, Y.-P., Olshevskaya, E., Pu, M., Dizhoor, A. M., and Pan, Z.-H. (2006). Ectopic expression of a microbial-type rhodopsin restores visual responses in mice with photoreceptor degeneration Neuron 50: 23-33. Lagali P S, Balya D, Awatramani G B, et. al. (2008). "Light-activated channels targeted to ON bipolar cells restore visual function in retinal degeneration". Nat. Neurosci. 11 (6): 667-75.

Therefore, there is a need of a systematic method for non-viral delivery of the ChR2 gene into retinal ganglion cells of the adult retina so as to create visually evoked potentials in the visual cortex. However, the two reported studies for restoration of vision in blind mice models involve delivery of ChR2 gene either by viral methods or by in-utero electroporation which is not applicable for in vivo applications. Further, no studies were found describing targeting of retinal ganglion cells specifically and effective behavioral improvement.

BRIEF SUMMARY OF THE INVENTION

The illustrated embodiments of the invention includes an in vivo method for sensitizing retinal ganglion cells in an eye without use of viral transfection includes the steps of nonviral in vivo delivering of gene coding for channelrhodospsin-2 (ChR2) or any photosensitive genetic material now known or later devised to target the retinal ganglion cells of a retina by intravitreous injection of plasmid DNA; and electroporating the plasmid into the retina. In addition to intravitreous injection of plasmid DNA or photosensitive genetic material, plasmid DNA or photosensitive genetic material may be inserted into the eye by ionotophoresis of the plasmids into the eye. Hereinafter any reference in this specification or claims to gene coding for channelrhodopsin-2 (ChR2) should be understood to include any photosensitive genetic material as well with such appropriate modifications as might be determined according to generally understood principles for biological application of the photosensitive genetic material.

The step of electroporating the plasmid into the retina includes the step of pulsed electroporating the plasmid into the retina.

The method further includes the steps of expressing ChR2 in retinal ganglion cells of the retina using specific promoters (e.g. Thy 1).

The method further includes the step of light activating ChR2 to evoke an action potential in the visual cortex leading to restoration of vision.

The step of nonviral in vivo delivering a channelrhodospsin-2 (ChR2) gene to target the retinal ganglion cells of a retina includes intravitreous injection of plasmid DNA (Thy 1-ChR2-YFP).

The method further includes the step of nonviral in vivo delivering a channelrhodopsin-2 (ChR2) gene to target the retinal ganglion cells of a retina by intravitreous injection of plasmid DNA and electroporating the plasmid into the retina includes treating macular degeneration, Leber's hereditary optic neuropathy, cone-rod dystrophy, Leber congenital amaurosis, Stargardt disease or retinitis pigmentosa.

The step of electroporating the plasmid into the retina includes producing an electric field in the retina by positioning one electrode with a negative polarity placed in contact with cornea of the eye, and by positioning an opposing electrode (positive) placed behind the eye in contact with the eye ball at least in part behind the retina. Alternatively, electroporation in humans can still be realized without surgically inserting an opposing electrode behind the eye by insertion of microelectrodes or wires adjacent to other locations in or near the eye ball. For example, larger electrodes can be placed peripheral to the eye or eye socket and still provide enough of a fringing electric field to obtain effective electroporation in the retina. Still further, a hollow conductive microwire can be inserted behind the eye near the vicinity of the retina and a conductive fluid expressed through the microwire which by electrical coupling to the microwire temporarily acts as an effective electrode for electroporation. The fluid is later absorbed by the body after the procedure is completed and the microwire removed.

The step of electroporating the plasmid into the retina includes producing an electric field in the retina includes positioning a cathode in contact with the cornea, and positioning an anode at least in part behind the retina.

The step of positioning a cathode in contact with the cornea includes positioning a hemispherical cathode in contact with the cornea.

The step of electroporating the plasmid into the retina includes applying an electric field across the eye in a range from approximately 1 V to 20 V at field strength of 1-2 V/mm in 5 to 20 of pulses in intervals of 5 pulses for pulse durations from approximately 20 to 50 ms.

The step of electroporating the plasmid into the retina includes pulsed electroporating the plasmid with optimized field strength amplitude, frequency, number of pulses, group repetition rate and duration of pulse and group repetition, which are optimized for transfection of the channelrhodospsin-2 (ChR2) gene into the retinal ganglion cells.

The illustrated embodiments also include an apparatus for in vivo electroporating plasmids into a retina of any eye which includes a first electrode with negative polarity placed in contact with a cornea of the eye, a second electrode with an opposite polarity placed behind the eye in contact with the eye ball at least in part behind the retina, and a pulsed voltage source coupled to the first and second electrodes for providing a pulsed DC voltage with an optimized field strength amplitude, frequency, number of pulses, group repetition rate and duration of pulse and group repetition, which are optimized for transfection of the channelrhodospsin-2 (ChR2) gene into the retinal ganglion cells. Optimization is realized through principles well known to the art and/or by experimentation.

The first electrode includes a cathode in contact with the cornea, and the second electrode includes an anode at least in part behind the retina.

The cathode in contact with the cornea includes a hemispherical cathode in contact with the cornea.

The voltage source generates an electric field across the eye in a range from approximately 1 V to 10 V at a field strength of 1-2 V/mm in 5 to 20 of pulses in intervals of 5 pulses for pulse durations from approximately 20 to 50 ms.

The first and second electrodes and voltage source are specifically arranged and configured for nonviral in vivo delivery of a channelrhodospsin-2 (ChR2) gene to the retinal ganglion cells of a retina by intravitreous injection of plasmid DNA and electroporation of the plasmid into the retina to treat macular degeneration, Leber's hereditary optic neuropathy, cone-rod dystrophy, Leber congenital amaurosis, Stargardt disease or retinitis pigmentosa.

The method of the illustrated embodiments of the invention aims to target the retinal ganglion cells and eliminates the need of using viral method. Therefore, the systematic approach of the illustrated embodiment of the invention has advantages of (1) in vivo nonviral delivery of the ChR2 gene; (2) targeting of retinal ganglion cells of the adult retina for efficient activation and better behavioral improvement and (3) use of image intensification devices for stimulating the retinal ganglion cells with ambient lighting conditions. The fundamental principle employed by the illustrated embodiment of the invention is that the gene coding ChR2 can be efficiently injected into retina by non-viral (electroporation) method and ChR2 can be made to express in retinal ganglion cells of retina by use of a promoter (e.g. Thy 1) and light activation of ChR2 expressed selectively in retinal ganglion cells of blind eye, will cause visually evoked potential in cortex leading to restoration of vision.

The disclosed approach of illustrated embodiment of the invention is an optogenetic treatment, which may be applicable to other causes of blindness such as macular degeneration, Leber's hereditary optic neuropathy, cone-rod dystrophy, Leber congenital amaurosis, Stargardt disease and similar diseases.

The illustrated embodiment of the invention is a method for optogenetic treatment of disease retinitis pigmentosa. This provides the ability to restore vision by eliciting electrophysiological responses in the visual cortex subsequent to light assisted stimulation of retinal ganglion cells after they have been transfected with a light sensitive protein, channelrhodospsin-2 (ChR2) using an electroporation method of delivery. The disclosed method comprises: 1) Specific targeting of retinal ganglion cells by use of the genetic construct with specific promoter (e.g. Thy 1) attached to the ChR2 gene; 2) Injection of the gene into the vitreous; 3) Efficient non-viral transfection of the retinal ganglion cells by electroporation, which requires administering an electric field of optimal strength, frequency and duration through the eye. The electric field is produced by positioning one hemispherical electrode placed gently in contact with the cornea, while the other electrode with a U-cut) placed in the back of the eye to accommodate the optic nerve and eye ball, 4) evaluation of the restoration/improvement of vision by behavioral tests and 5) use of image intensification devices, if necessary.

One purpose of the illustrated embodiment of the invention is to improve/restore vision in patients with retinitis pigmentosa and other eye related diseases. However, the immediate goal of the illustrated embodiment of the invention is to test the disclosed method in blind (rd1/rd1) mice by delivering Thy1-ChR2 coding genes into retinal ganglion cells of retina of adult mice via a nonviral electroporation method and to elicit visually evoked potential in cortex by pulsed light exposure and to restore vision as specifically determined by behavioral tests.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
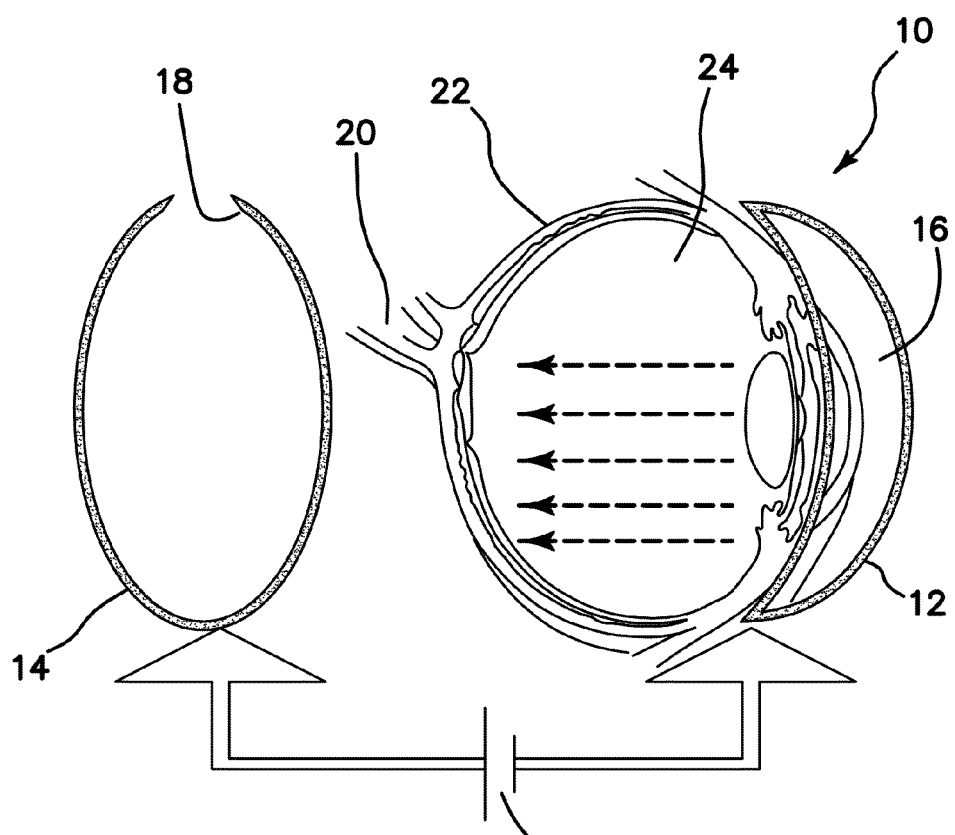
FIG. 1 is a diagram illustrating the apparatus of the invention whereby an electroporating field is impress across the eye and into the retina.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

In diseases such as Retinitis pigmentosa (RP), one of the most common forms of inherited retinal degeneration, progressive loss of photoreceptor cells occurs which eventually leads to blindness. Here, we disclose an in vivo method for efficient delivery of plasmids encoding light-sensitive proteins (ChR2) into the eye of small animal models having retinitis pigmentosa with the aim to restore vision. The illustrated delivery system is comprised of a hemi-spherical cathode to be placed on the cornea and an accommodating anode in back of the eye, driven by optimal electric pulses. Through electroporation of plasmids into a specific layer in the retina (e.g. promoter-specific to retinal ganglion cells), we eliminated the disadvantages of the viral delivery method such as safer administration and avoiding the difficulties in incorporating a large construct of promoter, ChR2, and a fluorescent protein marker into the lentivirus/Adeno associated virus. The specific layer of the retina which is the target of electroporation includes retinal ganglion cells and bipolar cells. Visually evoked potential (VEP) recording in cortex and the behavioral test confirmed functional recovery of vision in the retinitis pigmentosa mouse model (rd1/rd1).

Materials and Methods:
In-Vivo Transfection:
Transfection of retinal ganglion cells was achieved in rd1/rd1 mice by intravitreous injection of plasmid DNA (Thy 1-ChR2-YFP) followed by electroporation with a hemispherical cathode on the cornea and a hemisphere anode with a groove that slides around the optic nerve on the posterior surface of the eye. Since calcium phosphate and DEAE-dextran based transfection required chemicals to be inserted into the eye, the two least-damaging non-viral methods, namely, lipofection and electroporation for gene delivery were evaluated. Adult (6-8 weeks old) rd1/rd1 mice were treated humanely in strict compliance with IACUC on the use of animals in research. For lipofection experiments, plasmids were suspended in OMEM (Invitrogen) containing 400 μl/ml of Lipofectamine2000 (Invitrogen). Mixtures of plasmids and lipid containing media were incubated for 20 minutes at room temperature before injection. Before intravitreous injections, mice were anesthetized, pupils were dilated, and a sharpened tip of a sterilized micro-syringe was inserted through the sclera into the vitreous cavity. The injections were carried out with a 32-G needle of a Hamilton micro-syringe to deliver 1 μl of vehicle mixture.

The injection was relatively pain free: in order to prevent the animal from feeling pain during injection, both global and local anesthesia will be applied to the mice. The electric field strength administered through the eye was varied from 1 V to 10 V in intervals of 3V using a function generator. For each strength, the number of pulses was varied from 5 to 20 pulses (in intervals of 5 pulses) and for these conditions, two pulse durations (20 ms, 50 ms) were utilized. The treated animals were allowed to recover from anesthesia.

Retina Explant and Confocal Fluorescence Microscopy:

One to 2 weeks post-injection, the eyes were removed from the euthanized mice. The retinas were removed under the dissection microscope and cut into 200 μm square explants on a McIlwain tissue chopper. These were then placed into sterile 35-mm Petri dishes with a 14 mm central hole backed by a glass coverslip (MatTek). The explants were oriented ganglion cell side towards the coverslip. The Petri dishes were examined under the confocal fluorescence microscope (LSM 510, Zeiss) on a temperature controlled stage. For YFP excitation, 488 nm of Ar-Ion laser beam was used.

Opto-Electrophysiology Setup:

The electrical activity of individual ChR2-transfected retinal ganglion cells of the rd 1/rd 1 mice model in response to optical activation was monitored by patch-clamp measurements. The electrophysiology was developed on a Zeiss Axiovert microscope platform using an amplifier system (AM Systems Inc., USA). Parameters of the pipette puller were optimized in order to obtain desired borosilicate micropipettes of resistance from 3 to 5 MΩ for whole-cell patch clamping. The micropipette was filled with a solution containing (in mM) 130 K-Gluoconate, 7 KCl, 2 NaCl, 1 $MgCl_2$, 0.4 EGTA, 10 HEPES, 2 ATP-Mg, 0.3 GTP-Tris and 20 sucrose. The electrode was mounted on a XYZ motorized micromanipulator (Eppendorf Inc., USA). The output from the amplifier was digitized using a National Instruments card (PCI 6221). For electrophysiological recording, the hardware was interfaced with patch-clamp software from University of Strathclyde, UK. The whole system was built on a vibration isolation table (Newport Inc., USA) and electrical isolation was done by a home-made Faraday cage that was placed around the set up. For activation of ChR2-expressing cells (identified by YFP fluorescence), a blue (473 nm, 30 mW) diode laser beam illuminated the desired cell being patch-clamped. For electrophysiological measurements subsequent to optical activation, the diode laser pulses (generated using National Instruments PCI 6221 card) were synchronized with the patch clamp recording electrode.

In-Vivo Recording of Visually Evoked Potential (VEP) in Cortex:

The purpose of this procedure was to test if visually evoked potential (electrical activity of the neurons in the visual cortex) can be produced by activation of transfected retinal ganglion cells in the retina. This transmission of action potentials from the retinal ganglion cells to the cortex is an essential step for restoration of vision. For VEP recording, a linear midline skin incision was made following which a fine hole was made on the skull to allow the needle electrode to reach the cortex. Bipolar electrodes made from Teflon®-coated stainless steel wire was implanted stereotactically into the cerebral cortex bilaterally using standard coordinates. Continuous VEP is then recorded via an electroencephalogram amplifier (Biopac, Inc.) interfaced with acquisition software (Biopac, Inc.) on a networked personal computer. For activation of the eye expressing ChR2 as well as the control eye (non-treated), a blue (473 nm, 30 mW) diode laser was coupled to a 100 μm core optical fiber using a fiber coupler (Newport Inc., USA), mounted on a mechanical micromanipulator so as to position the tip of the fiber near one of the eyes. For generating and controlling pulses of light, the laser was interfaced with a personal computer. TTL pulses of the desired frequency (1 Hz to few Hz) were generated using the National Instruments (PCI 6221) card in order to generate required laser pulses for activation.

Behavioral Test:

In order to evaluate the optogenetic method for restoration of vision, a platform for light sensitive behavioral testing was designed for the Thy1-ChR2-YFP transfected rd1/rd1 mice. The behavioral test involves having the mice swim in a water maze where a platform is placed in a location near a light source from an array of light emitting diodes (Thorlabs Inc, USA) in the blue spectrum (460-470 nm). The purpose of this procedure was to ultimately test the improvement of vision in mice models having retinitis pigmentosa (rd1/rd1) after the retina is treated with the light sensitive protein, which will be indicated by the response of the mice towards the light source. Since the mice are swimming in the water maze, the platform provides a reward to them where they can rest instead of having to swim.

Results and Discussion:

Non-Viral Electroporation of Retina:

In order to restore photosensitivity in the retina with degenerated photoreceptors, retinal ganglion cells were transfected with channelrhodospsin-2 (ChR2 with specific promoter Thy1 and marker yellow florescent protein YFP) with the aim of restoring vision in the mouse model for retinitis pigmentosa (rd1/rd1). In contrast to the previous viral method for delivery of the ChR2 gene, we utilized a conventional non-viral electroporation method of delivering ChR2 genes specifically into retinal ganglion cells and examined the transfection efficacy of the electroporation method as compared to liposome mediated delivery. FIG. 1 depicts the schematic design of the prototype delivery system for the mouse eye 10. For electroporation, only plasmids were injected, following which the eye 10 was placed within a hemisphere cathode 12 on the cornea 16 and a hemisphere anode 14 with a groove 18 that slides around the optic nerve 20 on the posterior surface 22 of the eye 10. Anode 14 and cathode 12 are coupled to a voltage source 26. The ChR2 encoding gene is injected into the vitreous gel 24, before application of the electric field. The dotted arrows in FIG. 1 symbolically show the direction of movement of plasmids via electroporation. The use of the non-viral electroporation method removed the technical limitations on size of the construct (that can be inserted into the virus in case of viral delivery) and therefore promoters of any size can be in inserted into the construct. For the case of ChR2 based treatment of retinitis pigmentosa, it would be highly desirable to reinduce transgene expression by reinjection, and electroporation provides this opportunity.

Figure 2A:
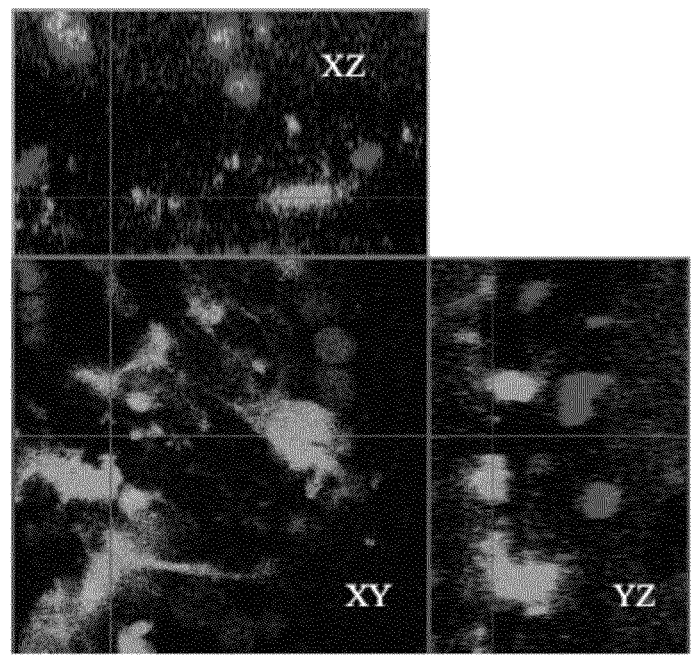
FIG. 2a is confocal imaging of YFP expression in the retinal explant from rd1/rd1 mouse (blind model) eye being treated with Thy1-ChR2-YFP by electroporation.
Figure 2B:
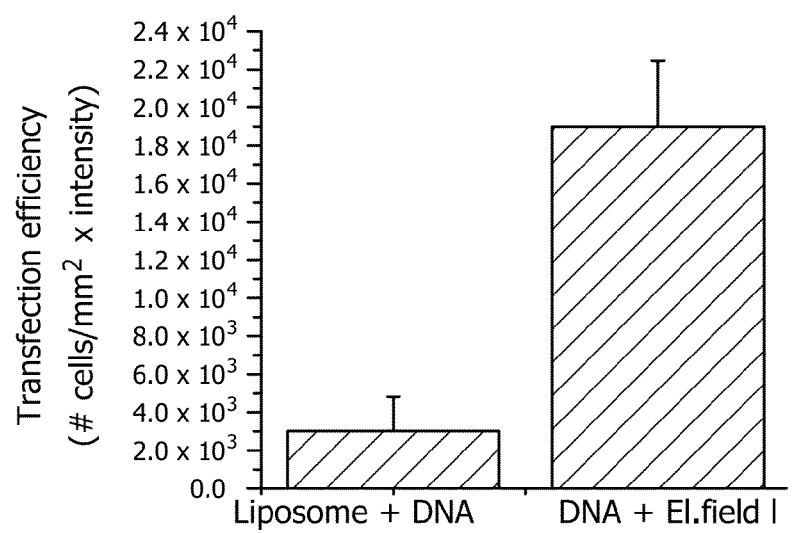
FIG. 2b shows increased efficiency of transfection by electric field mediated delivery as compared to lipofection.

Expression Analysis of In Vivo Delivery Via Lipofection and Electroporation:

Retinal ganglion cell-specific gene transfer is achievable with no lipid carrier and low power electroporation, which is believed to be less toxic to the retina as a whole. Confocal imaging of expressed YFP was carried out on the retinal explants from treated eyes at various time points after injection of plasmid (or plasmid-lipid complex) with and without electroporation. At 7 days after injection of Thy 1-ChR2-YFP in 1 µl of aqueous medium (OMEM), there was no identifiable gene (YFP) expression. In contrast, in all the eyes evaluated 7 days after injection of the same amount of plasmid combined with electroporation with few V/mm (e.g. 5V/mm, 10 pulses of 50 ms each separated by 100 ms), the marker fluorescent protein (YFP) expression was significant. FIG. 2a shows one of the retinal explants demonstrating strong YFP fluorescence in specific layer. While use of only lipofectamine led to very low level expression (FIG. 2b), use of lipofectamine with an electric field did not lead to significant improvement over the case where only the electric field is applied on naked plasmids.

Electroporation has been demonstrated to substantially increase transfection efficiency in several tissues. It is most easily applied to readily accessible tissues such as the skin and the eye, where it was first applied to the most accessible structure, the cornea. Subretinal injection of plasmid DNA combined with electroporation or subretinal injection of lipoplex had shown to result in efficient transgene expression. Though similar expression profile had been seen when adenoviral vectors were injected into the eye to transduce retinal cells, the transgene expression peaks within a few days and then declines and is generally undetectable by one month after injection. However, unlike adenoviral vectors, which are unable to substantially reinduce transgene expression by reinjection in rodents, electroporation injection are able to do so, providing an important advantage over adenoviral vectors.

Single Cell Electrophysiology of Light Activation of Retinal Ganglion Cells:

The electrical activity of individual ChR2-transfected retinal ganglion cells of the rd1/rd1 mice model in response to optical activation was monitored by patch-clamp measurements. Once the retina is extracted and examined for gene expression using confocal fluorescence microscopy, the single retinal ganglion cells were obtained by dissociating the explant on the coverslip. For functional testing of these cells, the cells were visualized first for fluorescence expression and then an electrode (in a glass micropipette) was inserted for patch clamping.

Figure 3:
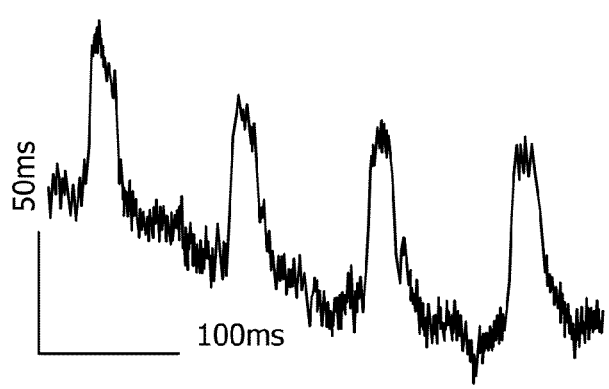
FIG. 3 is a graph of voltage verses time of the current-clamp measurements from a single retinal ganglion cell being treated with Thy1-ChR2-YFP and stimulated by 473 nm diode laser beam.

The ChR2-expressing retinal ganglion cell, exposed to 473 nm laser light was current clamped and FIG. 3 shows the action potentials from these sensitized cells subsequent to exposure to the laser light (100 ms separation). Repetitive potentials with different frequencies (in the range of a few Hz) could be generated by varying the frequency of the diode laser pulses. While fluorescence microscopy of marker fluorescent protein (YFP) confirmed specific expression in retinal ganglion cells (FIG. 2a), the patch clamp measurements subsequent to pulsed light (473 nm) irradiation showed the ability to optically stimulate the retinal ganglion cells.

Figure 4A:
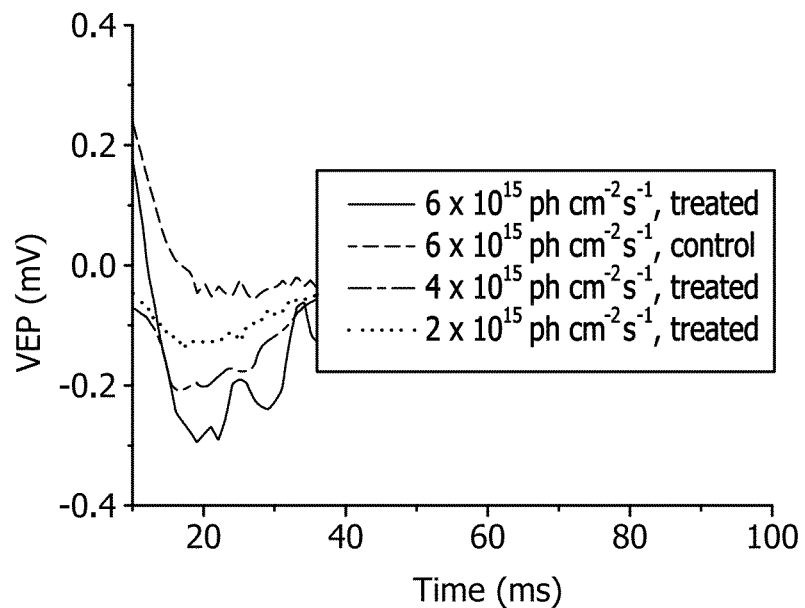
FIG. 4a is a graph of voltage verses time of a typical VEP recorded in cortex subsequent to stimulation of the blind-model eye being treated with Thy1-ChR2-YFP by electroporation.
Figure 4B:
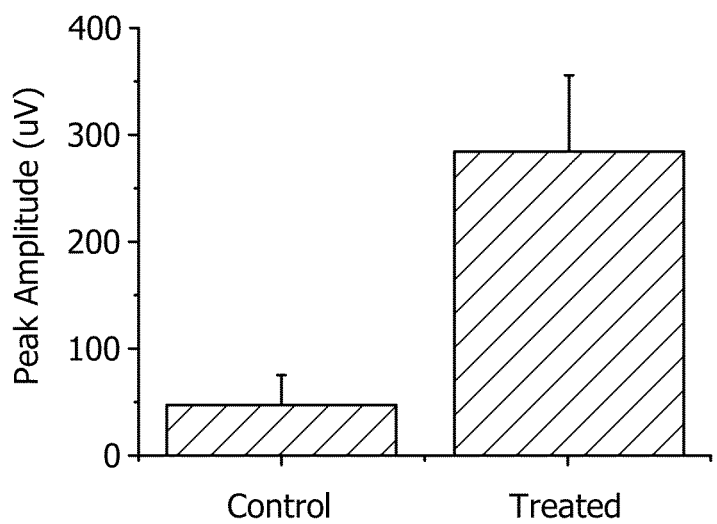
FIG. 4b shows comparison of peak amplitude of VEP for control and treated group at various photon flux.

In-Vivo Recording Confirmed Light-Activated VEP in the Cortex:

In-vivo functional measurements were performed on an in-vivo rodent model (rd1/rd1). After 1-2 weeks of injection, while under anesthesia the mice were placed under a stereotactic unit and an EEG electrode was placed in order to test for visually evoked potentials in the cortex. The purpose of this procedure was to test if visually evoked potential (electrical activity of the neurons in the visual cortex) can be produced by activation of transfected retinal ganglion cells in the retina. This transmission of action potentials from the retinal ganglion cells to the cortex is an essential step for restoration of vision. A typical VEP (averaged over one hundred stimulation pulses) recorded subsequent to stimulation of the eye (after one week of treatment with Thy1-ChR2-YFP) by the blue diode laser beam is shown in FIG. 4a. Illumination of the non-treated eye with similar laser power did not lead to a detectable VEP that can be correlated to the applied laser pulses (FIG. 4b). The VEP signal represents the first step towards transmission of activated potential from the targeted retinal ganglion cells to the visual cortex, thus providing the possibility of restoration of vision by optogenetic stimulation.

Effect of Improved Light Sensitivity of the Retina on Mouse Behavior:

The mice with restored vision (eye treated by electroporation of Thy1-ChR2-YFP) were able to respond to the light emitted from the LEDs and were able to reach the platform faster than an untreated mouse. The behavior of the treated mice was found to depend on intensity of the activation light with a threshold intensity (or distance) from where treated mouse could respond to the light. For differentiating the memory-associated improvements (regarding platform position as a point of reward) in behavior of the swimming mice versus true vision restoration, we changed the position of the light source with respect to the platform for individual mice. Preliminary results showed that the treated mouse (with restored vision) is able to reach the platform faster than the untreated counterpart or itself (before treatment). Further, the mice near the diverging source were seen to react to the light beam more efficiently (i.e. faster movement). The intensity of the diverging light was varied so as to determine the minimum distance from where the mice can respond to light.

CONCLUSION

Restoration of vision was achieved by use of an in vivo nonviral electroporation method for efficient delivery of plasmids encoding light-sensitive proteins (ChR2) into the eye of small animal models having retinitis pigmentosa. The parameters of the electric pulses (amplitude, frequency, number of pulses and duration) in the delivery system was optimized. Through electroporation of plasmids into a specific layer in the retina (e.g. promoter-specific to retinal ganglion cells), we eliminated the disadvantages of the viral delivery method. Visually evoked potential recording in cortex and the behavioral test confirmed functional recovery of vision in the retinitis pigmentosa mouse model (rd1/rd1).

Although transfection of ChR2 into cells in retina could induce electrical activity in cortex in rd1/rd1 (blind) mice under intense blue diode laser illumination, the threshold light intensity required to evoke visual potentials in ChR2-transfected cells is much higher than ordinary lighting conditions. In case of lack of restoration of vision after optogenetic treatment under ordinary lighting conditions, image intensification devices will be used for stimulating the retinal ganglion cells with ambient lighting conditions.

We believe our method of nonviral delivery of gene encoding light-sensitive proteins will pave the way for in-vivo applications in circuit specific intervention of retinal diseases such as macular degeneration, Leber's hereditary optic neuropathy, cone-rod dystrophy, Leber's congenital amaurosis, Stargardt's disease in humans. Although the illustrated embodiment has been disclosed in terms of a rat model, it is expressly contemplated that the apparatus and method of the invention is to be applied with appropriate modifications to human subjects.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for in vivo electroporation of a plasmid into a retina of an eye comprising:
    a first electrode comprising a cathode with a negative polarity, wherein the first electrode is capable of being placed in contact with a cornea of the eye;
    a second electrode comprising an anode with a positive polarity and a groove, wherein the groove is configured to slide around the optic nerve and place the second electrode in a posterior position to the eye ball to provide an electrical field between the first and second electrode extending at least in part to the retina; and
    a pulsed voltage source coupled to the first and second electrodes for providing a pulsed DC voltage with an optimized field strength amplitude, frequency, number of pulses, group repetition rate and duration of pulse and group repetition, wherein the first and second electrodes are optimized for transfection of the plasmid encoding channel rhodospsin-2 (ChR2) gene or a plasmid comprising a gene encoding photosensitive ion channel proteins into retinal ganglion cells located at the periphery of the retina.

2. The apparatus of claim 1 where the cathode capable of being in contact with the cornea comprises a hemispherical cathode capable of being in contact with the cornea.

3. The apparatus of claim 1 where the voltage source generates an electric field across the eye in a range from approximately 1 V to 20 V at a field strength of 1-2 V/mm in 5 to 20 of pulses in intervals of 5 pulses for pulse durations from approximately 20 to 50 ms.

4. The apparatus of claim 1, further comprising a noninvasive image intensification device for stimulating the retinal ganglion cells in vivo with ambient light.

* * * * *